(12) United States Patent
Ergler et al.

(10) Patent No.: US 10,429,524 B2
(45) Date of Patent: Oct. 1, 2019

(54) X-RAY DETECTOR WITH NON-TRANSPARENT INTERMEDIATE LAYER

(71) Applicant: Siemens Healthcare GmbH, Erlangen (DE)

(72) Inventors: Thorsten Ergler, Erlangen (DE); Miguel Labayen De Inza, Forchheim (DE); Stefan Woelfel, Dormitz (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 281 days.

(21) Appl. No.: 15/622,555

(22) Filed: Jun. 14, 2017

(65) Prior Publication Data

US 2017/0363754 A1 Dec. 21, 2017

(30) Foreign Application Priority Data

Jun. 20, 2016 (DE) .................. 10 2016 210 935

(51) Int. Cl.
*G01T 1/24* (2006.01)
*H01L 27/146* (2006.01)
*A61B 6/03* (2006.01)
*A61B 6/00* (2006.01)

(52) U.S. Cl.
CPC .............. *G01T 1/244* (2013.01); *A61B 6/032* (2013.01); *A61B 6/42* (2013.01); *G01T 1/242* (2013.01)

(58) Field of Classification Search
CPC ....... A61B 6/037; A61B 6/482; A61B 6/4241; A61B 6/4208; A61B 6/00; A61B 6/4258; A61B 6/485; G01T 1/244; G01T 1/247; H01L 27/1469; H01L 27/14676; H01L 27/14623
See application file for complete search history.

(56) References Cited

U.S. PATENT DOCUMENTS

| 2009/0224162 A1 | 9/2009 | Inuiya |
| 2015/0168569 A1 | 6/2015 | Hackenschmied et al. |
| 2019/0004191 A1* | 1/2019 | Cao ........................... G01T 1/24 |

FOREIGN PATENT DOCUMENTS

| DE | 102012213411 A1 | 2/2014 |
| DE | 102015216527 B3 | 10/2016 |
| WO | WO 20170036619 A1 | 3/2017 |

OTHER PUBLICATIONS

German Office Action 10 2016 210 935.9 dated Mar. 1, 2017.

* cited by examiner

*Primary Examiner* — Don K Wong
(74) *Attorney, Agent, or Firm* — Harness, Dickey & Pierce, P.L.C.

(57) ABSTRACT

An X-ray detector includes a direct-converting converter element, an evaluation unit, and an intermediate layer arranged flat between the direct-converting converter element and the evaluation unit. In an embodiment, the intermediate layer is non-transparent for visible, infrared, or ultraviolet light.

22 Claims, 2 Drawing Sheets

X-RAY DETECTOR WITH NON-TRANSPARENT INTERMEDIATE LAYER

PRIORITY STATEMENT

The present application hereby claims priority under 35 U.S.C. § 119 to German patent application number DE 102016210935.9 filed Jun. 20, 2016, the entire contents of which are hereby incorporated herein by reference.

FIELD

At least one embodiment of the invention generally relates to an X-ray detector and a medical device.

BACKGROUND

In the field of X-ray imaging, for example in computer tomography, angiography, or radiography, use can be made of counting direct-converting X-ray detectors or integrating indirect-converting X-ray detectors.

In direct-converting X-ray detectors, the X-ray radiation or the photons can be converted in to electrical pulses by a suitable converter material of the converter element. As direct-converting converter material, the following can be used for example: CdTe, CZT, CdZnTeSe, CdTeSe, CdMnTe, InP, $TlBr_2$, $HgI_2$, GaAs or others. The electrical pulses are evaluated by evaluation electronics, for example by an integrated circuit (Application Specific Integrated Circuit, ASIC).

In counting direct-converting X-ray detectors, incident X-ray radiation is measured by counting the electrical pulses which are triggered by the absorption of X-ray photons in the converter material. As a rule, the amount of the electrical pulse is proportional to the energy of the absorbed X-ray photon. This means that spectral information can be extracted by comparing the amount of the electrical pulse with a threshold value.

For the purpose of signal stabilization, the converter element, for example having CdZnTe, CdTe, CdHgTe, CMT, or the like, can be illuminated with additional electromagnetic radiation, for example visible light, IR or UV light. The illumination results in the formation of electron-hole pairs which flow away via the converter material and can contribute to an offset signal. By using the additional illumination, an improved short-term and long-term stability of the X-ray detector can be achieved.

Visible, infrared, ultraviolet, or long-wavelength light can pass through the converter material and emerge from the converter element on the side of the converter element facing away from the illumination source. The evaluation unit is generally located on the side facing away from the illumination source so that a light quantity of the additional illumination can penetrate the evaluation unit.

Optical photons can be absorbed in the converter element or can be reflected at the surface on the side of the converter element facing the illumination source so that they do not penetrate the converter element. Optical photons can be absorbed in an electrode on the side of the converter element facing away from the illumination source. Optical photons can penetrate directly, following scattering or reflection, in to the evaluation unit and interact with the evaluation unit. The evaluation unit can have amplifier structures with typically small capacitance which react very sensitively to the additional illumination. For example, electron-hole pairs can be generated directly in amplifying diode structures.

An X-ray detector is known from the as yet unpublished patent application 102015216527.2, the entire contents of which are incorporated herein by reference, which has a substrate with an electrically conducting connection between a readout contact in the region of the top side of the substrate and an input of a preamplifier in an active layer of an integrated circuit. A first electrically conducting connection is provided between the readout contact and a second electrically conducting connection. An area of a first light shield at the top side of the substrate is larger than an area of an optically transparent region in the substrate that is laterally delimited by a second light shield so that the area of the first light shield covers the area of the optically transparent region in a first projection along the surface normal. The second electrically conducting connection is provided inside a second projection of the area of the optically transparent region along the surface normal and below the second light shield. A third electrically conducting connection between the second electrically conducting connection and the preamplifier is provided below the second light shield.

SUMMARY

At least one embodiment of the invention discloses an X-ray detector, and at least one embodiment of the invention discloses a medical device, which enable a shielding of the evaluation unit against the incidence of the additional illumination.

At least one embodiment of the invention is directed to an X-ray detector and at least one embodiment of the invention is directed to a medical device.

At least one embodiment of the invention relates to an X-ray detector including a direct-converting converter element, an evaluation unit and/or a readout unit, and an intermediate layer arranged flat between the direct-converting converter element and the evaluation unit and/or a readout unit, wherein the intermediate layer is non-transparent for visible, infrared, or ultraviolet light.

At least one embodiment of the invention further relates to a medical device including at least one embodiment of the inventive X-ray detector. Advantageously the advantages of at least one embodiment of the inventive X-ray detector can be transferred to the medical device. Advantageously the imaging properties of the system, in particular noise contributions and stability of the behavior of the X-ray detector, can be improved.

BRIEF DESCRIPTION OF THE DRAWINGS

Example embodiments of the invention are explained in detail below on the basis of drawings. In this regard, in the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector including a direct-converting converter element, an evaluation unit and/or a readout unit, and an intermediate layer arranged flat between the direct-converting converter element and the evaluation unit and/or a readout unit, wherein the intermediate layer is non-transparent for visible, infrared, or ultraviolet light.

The converter element and the evaluation unit can be interconnected in a stacked construction. The evaluation unit can have evaluation electronics, for example an integrated circuit, in a substrate. The direct-converting converter element and the evaluation unit can have at least one contact or one electrode which can be interconnected in an electrically conducting manner, for example by using a solder connection. Preferably the converter element and the evaluation unit can have a plurality of contacts which preferably have the same distribution or the same pattern with for example the same spacings on the converter element and the evaluation unit so that the contacts of the converter element and the contacts of the evaluation unit can lie congruently one above the other in a stacked construction. The converter element and the evaluation unit can have the same quantity of contacts. The converter element and the evaluation unit can have a pixel-like structure.

The intermediate layer can be a so-called underfill. Following the electrically conducting interconnection of the converter element and the evaluation unit, the intermediate layer can be introduced, in a flowable state, in to the space formed between same. The intermediate layer can solidify or harden after being introduced. In particular the intermediate layer can be hardened in a thermal process. The intermediate layer can have an intermediate layer material. The intermediate layer or the intermediate layer material can have a viscosity, for example in the flowable state, between 3300 mPa·s and 65000 mPa·s. The intermediate layer material can be processed or introduced in a flowable state in particular at a temperature in the range from 50° C. to 90° C.

The intermediate layer is arranged flat between the converter element and the evaluation unit. The converter element, the intermediate layer, and the evaluation unit can form a stacked construction. The flat arrangement of the intermediate layer can mean that the intermediate layer extends essentially over the entire extent of the interface to the evaluation unit and the interface to the converter element. The intermediate layer can have an extent that differs from the converter element and/or from the evaluation unit.

The converter element can be illuminated with visible, infrared, or ultraviolet light by an additional illumination. The wavelength of the light can lie between 600 nm and 1000 nm, preferably 850±15 nm.

The intermediate layer is non-transparent for the light from the additional illumination so that the electronic components of the evaluation unit are not influenced by the additional illumination. The intermediate layer can preferably be non-transparent for wavelengths in the range from 850±15 nm. The intermediate layer can be at least partly non-transparent over its surface area. The intermediate layer can be uniformly non-transparent. The intermediate layer can have a uniform layer thickness. The intermediate layer can be non-transparent along its entire extent. Die intermediate layer can preferably be completely non-transparent. The non-transparency can preferably prevent or reduce light from the additional illumination passing through in the direction of the stacked construction toward the evaluation unit. The intermediate layer can be optically non-transparent, wherein the intermediate layer can be non-transparent in particular for the light from the additional illumination. Essentially no light from the additional illumination or less than 10 percent of the light quantity of the additional illumination can pass through the intermediate layer. Essentially the intermediate layer can be non-transparent in such a manner that the electronic components, for example input capacitors, experience little or no influence from the additional illumination.

The non-transparency of the intermediate layer can be predetermined by a selection of parameters, for example an absorption coefficient and/or a reflection coefficient, a layer thickness, an intermediate layer material, a possible filling material, or a concentration of the filling material. Advantageously, the desired non-transparency of the intermediate layer can be predetermined by means of a suitable combination of the parameters. The non-transparency can be achieved by absorbing and/or reflecting the light from the additional illumination.

The absorption coefficient can be specified as a spectral absorption coefficient $\alpha(\lambda)$ and the reflection coefficient as a spectral reflection coefficient $\rho(\lambda)$, wherein there is a dependency on the wavelength $\lambda$. The spectral transmittance is given by $\tau(\lambda)=1-\rho(\lambda)-\alpha(\lambda)$. The spectral transmittance, in particular for the wavelengths in the range from $850\pm15$ nm, can be at most 0.1, preferably 0.05, especially preferably 0.01, and in particular preferably 0. The layer thickness can lie in the range from 60 μm to 280 μm. The layer thickness can be dependent on a size or a height of the solder connections.

The size or the height of the solder connections can define the spacing between the converter element and the evaluation unit. The layer thickness can correspond to the spacing. For example, the layer thickness can be defined by the spacing between the converter element and the evaluation unit, and the parameters absorption coefficient and/or reflection coefficient can be selected in such a manner that the intermediate layer is non-transparent.

Advantageously, the intermediate layer can be optimized by a suitable choice of the parameters so that the intermediate layer satisfies the requirements placed on the viscosity in the flowable state for example. The intermediate layer can advantageously have the same or better mechanical, electrical, and thermal properties as compared with a transparent intermediate layer.

The inventors recognized that introducing an optically non-transparent intermediate layer between the converter element and the evaluation unit can shield the sensitive structures of the evaluation unit from optical photons, for example in the visible, IR, or UV range. The intermediate layer can deliver a mechanical stabilization and additionally a shielding of the evaluation unit from the additional illumination.

In this regard, the material of the intermediate layer can be adapted as to optical or coloring respects to the necessary optical absorption rate or the desired reflecting power. The intermediate layer can be optimized or adapted by means of additives or a color-adapted selection of material to the blocking or shielding of a specific range of wavelengths, in particular the wavelength of the additional illumination. Advantageously diodes with small implant structures or fine MOS-FET elements can be shielded from the influence due to incident additional illumination. Advantageously small input capacitances can be achieved in the evaluation unit.

Advantageously the light quantity of the additional illumination can be absorbed at least partly. Advantageously the sensitive structures in the evaluation unit can be shielded from the additional illumination. The inventors recognized that, as a result of a non-transparent intermediate layer, small capacitances of the initial amplifier stages of the amplifier structure in the evaluation unit can be advantageously maintained and that the electronics noise in the evaluation unit can be advantageously unaffected by the intermediate layer. Advantageously changes in the design of the evaluation unit can be avoided. Shielding metal layers in the evaluation unit can be advantageously reduced or avoided.

According to an embodiment of the invention, the converter element and the evaluation unit are connected by at least one solder connection and the at least one solder connection is partly enclosed by the intermediate layer.

The intermediate layer can enclose the electrically conducting connections, in particular solder connections, between the converter element and the evaluation unit. The intermediate layer can incorporate the electrically conduction connections. The electrically conducting connections, in particular solder connections, can be configured as completely non-transparent. The solder connections can shield the light of the additional illumination from the evaluation unit. The intermediate layer can have an increased non-transparency in the body of the solder connection as compared with the body of the intermediate layer without a solder connection. At the interface of the solder connection to the intermediate layer, in particular close to the converter element, a light quantity of the additional illumination can be scattered.

Advantageously the intermediate layer can absorb the scattered light quantity. Advantageously the intermediate layer can form a continuous flat extended layer with the solder connection. Advantageously the intermediate layer and the solder connection can be non-transparent. Advantageously the volumes between adjacent solder connections can be configured as non-transparent via of the intermediate layer.

According to an embodiment of the invention, the X-ray detector furthermore has an illumination unit for illuminating the converter element with visible, infrared, or ultraviolet light. The illumination unit can be an LED for example. The illumination unit can be configured in such a manner for example that the converter element can be illuminated from the direction of incidence of the X-ray radiation. Advantageously the signal for the X-ray detector can be stabilized, in particular with respect to time. Alternatively the additional illumination can be emitted by an external illumination unit outside the X-ray detector.

According to an embodiment of the invention, the intermediate layer shields the evaluation unit from at least 90 percent of a light quantity falling on to the intermediate layer from the illumination unit. The intermediate layer preferably shields the evaluation unit from at least 95 percent, especially preferably at least 99 percent, and in particular preferably 100 percent of the light quantity falling on to the intermediate layer. Advantageously the electronic components of the evaluation unit can be shielded from the incidence of the additional illumination.

Advantageously the influence of the additional illumination on the electronic components of the evaluation unit can be reduced or avoided. The non-transparency of the intermediate layer can be adjusted or defined by using absorption properties and/or reflection properties of the intermediate layer, in particular for visible, infrared, or ultraviolet light.

According to an embodiment of the invention, the intermediate layer absorbs the light at least partly. Advantageously a refection or scattering at the evaluation unit or the solder connections can be avoided as a result of the absorption.

According to an embodiment of the invention, the intermediate layer reflects at least partly the light falling on to it. Advantageously the light, in particular close to the interface to the converter element, can be reflected for example in such a manner that the light is reflected toward the converter element again so that the light cannot propagate farther in the direction of the evaluation unit. Advantageously a combination of absorption and reflection can be selected to combine the advantages.

According to an embodiment of the invention, the intermediate layer has an epoxide compound or a prepolymer. In particular, the intermediate layer or the intermediate layer material can have an epoxy resin. At the moment when the intermediate layer is introduced in to the gap between the converter element and the evaluation unit, the material of the intermediate layer, for example having an epoxide compound, an epoxy resin, or a prepolymer, can be liquid or flowable.

Advantageously the intermediate layer can harden, for example under the effect of temperature. The intermediate layer can advantageously increase the mechanical stability of the stacked construction. The intermediate layer can advantageously increase the stability with respect to temperature changes.

According to an embodiment of the invention, the intermediate layer has a filling material. The intermediate layer material can have a filling material. The filling material can have a low, in particular thermal, expansion coefficient. The filling material can have for example Al2O3, SiO2, BN, AlN, TiN, TiO2, PZT (PbZrTiO3), ZrO2, or YSZ (so-called yttria-stabilized zirconia). The filling material can be non-transparent for infrared, visible, or ultraviolet light, for example wavelengths in the range between 600 nm and 1000 nm, preferably 850±15 nm. The filling material can contribute advantageously to the mechanical stability of the stacked construction. The filling material can contribute advantageously to the non-transparency of the intermediate layer. The concentration of the filling material can be chosen in such a manner that the viscosity of the intermediate layer material, for example in the flowable state, lies between 3300 mPa·s and 65000 mPa·s. In particular the diameter or the size of the filling material particles of the filling material can be smaller than the spacing between the converter element and the evaluation unit, for example less than 10 percent of the spacing.

According to an embodiment of the invention, the intermediate layer has colored particles. The intermediate layer material can have colored particles. For example the colored particles can have carbon of one of the various organic/metal complexes or TiO2. The colored particles can be a filling material particle. Advantageously the non-transparency can be adjusted by the addition of colored particles. The colored particles can be non-transparent for infrared, visible, or ultraviolet light, for example wavelengths in the range between 600 nm and 1000 nm, preferably 850±15 nm.

According to an embodiment of the invention, the converter element has cadmium. The converter element can have CdZnTe, CdTe, or CdHgTe. Advantageously the converter element can be suitable for the conversion of X-ray beams in the field of medical X-ray imaging.

At least one embodiment of the invention further relates to a medical device including at least one embodiment of the inventive X-ray detector. Advantageously the advantages of at least one embodiment of the inventive X-ray detector can be transferred to the medical device. Advantageously the imaging properties of the system, in particular noise contributions and stability of the behavior of the X-ray detector, can be improved.

According to an embodiment of the invention, the medical device is a computer tomograph. Advantageously layer images and three-dimensional or four-dimensional volume images can be reconstructed with the aid of the measurement data from the X-ray detector.

Figure 1:
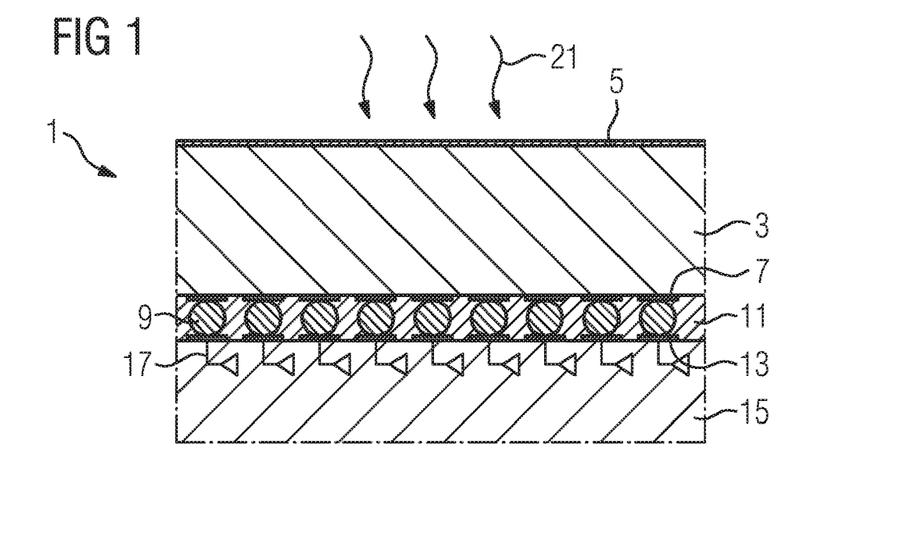
FIG. 1 shows a concept in schematic form of an inventive X-ray detector according to a first embodiment.

FIG. 1 shows an example implementation of the inventive X-ray detector 1 according to a first embodiment. The X-ray detector 1 has a direct-converting converter element 3, an evaluation unit 15, and an intermediate layer 11 arranged flat between the direct-converting converter element 3 and the evaluation unit 15, wherein the intermediate layer 11 is non-transparent for visible, infrared, or ultraviolet light. The converter element 3 has, on the side of incidence for X-ray radiation 21 which corresponds to the top side in the figure, a top electrode 5. On the opposite side to the top electrode 5, the converter element 3 has contacts 7. The evaluation unit 15 has contacts 13 on the side facing the converter element 3. The contact 7 on the converter element 3 and the contact 13 on the evaluation unit 15 are connected by at least one solder connection 9 and the at least one solder connection 9 is partly enclosed by the intermediate layer 11. An amplifier structure 17 in the evaluation unit 15 is located in an electrically conducting connection with the contact 13.

Figure 2:
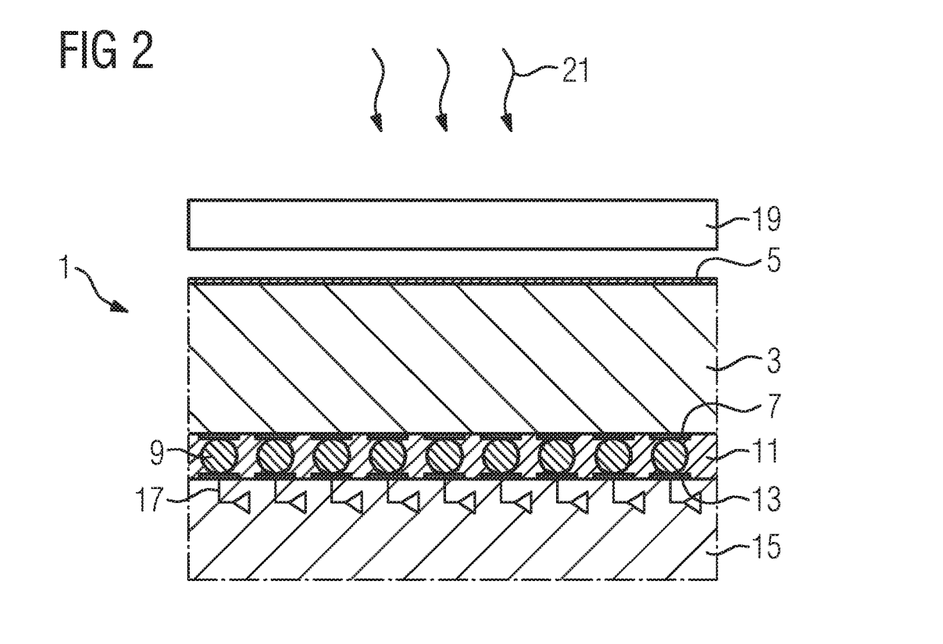
FIG. 2 shows a concept in schematic form of an inventive X-ray detector according to a second embodiment.

FIG. 2 shows an example implementation of the inventive X-ray detector 1 according to a second embodiment. The X-ray detector 1 furthermore has an illumination unit 19 for illuminating the converter element 3 with visible, infrared, or ultraviolet light. The illumination unit 19 can have a mechanical connection to the converter element 3 (not shown).

Figure 3:
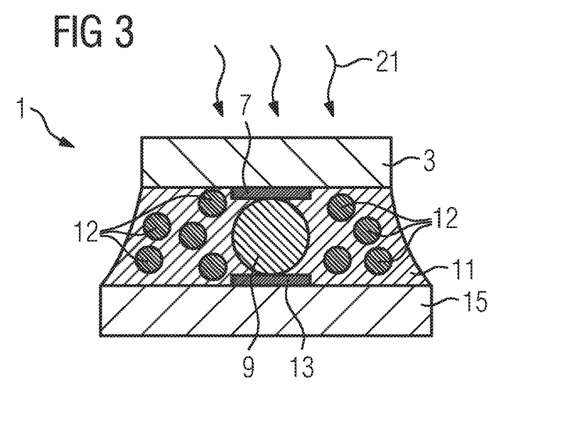
FIG. 3 shows a concept in schematic form of an inventive X-ray detector according to a third embodiment.

FIG. 3 shows an example implementation of the inventive X-ray detector 1 according to a third embodiment. The intermediate layer 11 has a filling material 12. The filling material 12 has a low, in particular thermal, expansion coefficient. The filling material 12 is non-transparent for infrared light, in particular wavelengths in the range from 850±15 nm. The concentration of the filling material 12 is chosen in such a manner that the viscosity of the intermediate layer material, for example in the flowable state, has a viscosity between 3300 mPa·s and 65000 mPa·s. The intermediate layer material can be processed or introduced in a flowable state in particular at a temperature in the range from 50° C. to 90° C. The diameter or the size of the filling material particles of the filling material 12 is in particular smaller than the spacing between converter element 3 and the evaluation unit 15, for example smaller than 10 percent of the spacing. The filling material 12 can have Al2O3, SiO2, BN, AlN, TiN, TiO2, PZT (PbZrTiO3), ZrO2, or YSZ (so-called yttria-stabilized zirconia). The intermediate layer 11 or the filling material 12 can have colored particles. The colored particles can have for example carbon of one of the various organic/metal complexes or TiO2. The colored particles can be filling material particles. The colored particles can be non-transparent in particular for infrared light, in particular wavelengths in the range from 850±15 nm, or absorb or reflect these wavelengths. The flat area extent of the converter element 3 and the flat area extent of the evaluation unit 15 can be different. The intermediate layer 11 can be delimited laterally by means of concave areas.

Figure 4:
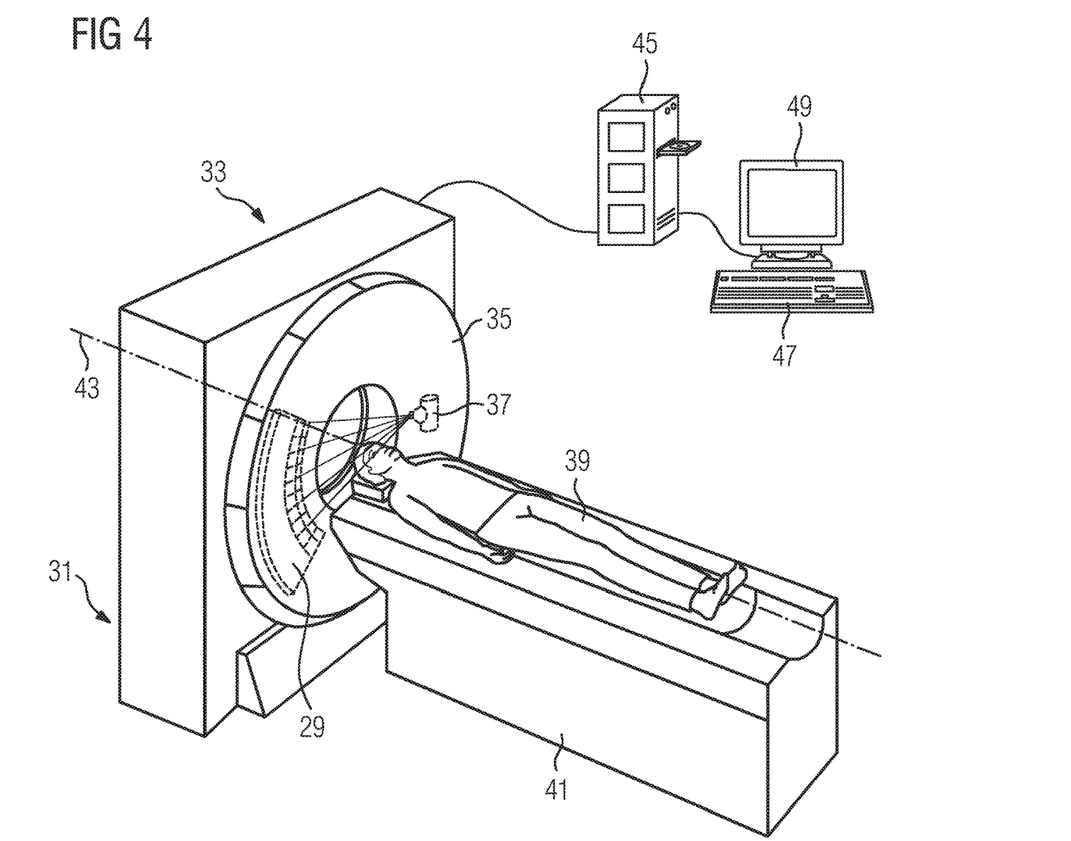
FIG. 4 shows a concept in schematic form of an inventive computer tomograph.

FIG. 4 shows an example embodiment of the inventive computer tomograph 31 with a detector apparatus 29. The detector apparatus 29 has the inventive X-ray detector 1. The computer tomograph 31 contains a gantry 33 with a rotor 35. The rotor 35 incorporates an X-ray source 37 and the inventive detector apparatus 29. The patient 39 is lying down on the patient bed 41 and can be moved along the rotational axis z 43 through the gantry 33. For the purpose of controlling and calculating the cross-sectional images, use is made of an arithmetic unit 45. An input facility 47 and an output apparatus 49 are connected to the arithmetic unit 45.

Although the invention has been closely illustrated in detail by means of the preferred example embodiment, the invention is not limited by the examples disclosed, and other variations can be derived from same by a person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector comprising:
   a direct-converting converter element;
   an evaluation unit; and
   an intermediate layer arranged flat between the direct-converting converter element and the evaluation unit, the intermediate layer being non-transparent for visible, infrared, or ultraviolet light.

2. The X-ray detector of claim 1, wherein the direct-converting converter element and the evaluation unit are connected by at least one solder connection and wherein the at least one solder connection is partly enclosed by the intermediate layer.

3. The X-ray detector of claim 1, further comprising:
   an illumination unit to illuminate the converter element with visible, infrared, or ultraviolet light.

4. The X-ray detector of claim 3, wherein the intermediate layer is configured to shield the evaluation unit, from at least 90 percent of a light quantity falling on to the intermediate layer, from the illumination unit.

5. The X-ray detector of claim 1, wherein the intermediate layer is configured to at least partly absorb the light.

6. The X-ray detector of claim 1, wherein the intermediate layer is configured to at least partly reflect the incident light.

7. The X-ray detector of claim 1, wherein the intermediate layer includes an epoxide compound or a prepolymer.

8. The X-ray detector of claim 1, wherein the intermediate layer includes a filling material.

9. The X-ray detector of claim 1, wherein the intermediate layer includes colored particles.

10. The X-ray detector of claim 1, wherein the converter element includes cadmium.

11. A medical device, comprising:
    the X-ray detector of claim 1.

12. The medical device of claim 11, wherein the medical device is a computer tomograph.

13. The X-ray detector of claim 2, further comprising:
    an illumination unit to illuminate the converter element with visible, infrared, or ultraviolet light.

14. The X-ray detector of claim 13, wherein the intermediate layer is configured to shield the evaluation unit, from at least 90 percent of a light quantity falling on to the intermediate layer, from the illumination unit.

15. The X-ray detector of claim 2, wherein the intermediate layer is configured to at least partly absorb the light.

16. The X-ray detector of claim 2, wherein the intermediate layer is configured to at least partly reflect the incident light.

17. A medical device, comprising:
    the X-ray detector of claim 2.

18. The X-ray detector of claim 2, wherein the intermediate layer is configured to be non-transparent for wavelengths in the range from 850±15 nm.

19. The X-ray detector of claim 3, wherein the intermediate layer is configured to at least partly absorb the light.

20. The X-ray detector of claim 3, wherein the intermediate layer is configured to at least partly reflect the incident light.

21. A medical device, comprising:
    the X-ray detector of claim 3.

22. The X-ray detector of claim 3, wherein the intermediate layer is configured to be non-transparent for wavelengths in the range from 850±15 nm.

* * * * *